United States Patent [19]
Keaney

[11] Patent Number: 5,713,349
[45] Date of Patent: Feb. 3, 1998

[54] INHALATION THERAPY

[76] Inventor: Niall Keaney, Fyndoune Mews, Durham DH1 5RJ Hartside, United Kingdom

[21] Appl. No.: 557,113

[22] PCT Filed: Jun. 2, 1994

[86] PCT No.: PCT/GB94/01208

§ 371 Date: Jan. 31, 1996

§ 102(e) Date: Jan. 31, 1996

[87] PCT Pub. No.: WO94/27664

PCT Pub. Date: Dec. 8, 1994

[30] Foreign Application Priority Data

Jun. 2, 1993 [GB] United Kingdom ............... 9311395

[51] Int. Cl.[6] ........................................... A61M 16/00
[52] U.S. Cl. ........................ 128/204.23; 128/204.21; 128/204.18
[58] Field of Search ............... 128/204.21, 204.23, 128/204.24, 204.26, 207.18, 204.18

[56] References Cited

U.S. PATENT DOCUMENTS 4,648,395  3/1987  Sato et al. .

FOREIGN PATENT DOCUMENTS

| 0178925 | 4/1986 | European Pat. Off. . |
| 1568808 | 6/1980 | United Kingdom . |
| WO 89/06147 | 7/1989 | WIPO . |
| WO 92/07599 | 5/1992 | WIPO . |
| WO 92/15353 | 9/1992 | WIPO . |
| WO 93/00952 | 1/1993 | WIPO . |

*Primary Examiner*—Vincent Millin
*Assistant Examiner*—William J. Deane, Jr.
*Attorney, Agent, or Firm*—Galgano & Burke

[57] ABSTRACT

This invention relates to a device for controlling the delivery of therapeutic respiratory agents to the respiratory system of a patient. The device includes a drug delivery means which is extremely controlled by a fluid flow control means in response to the respiratory cycle of the patient. The device is so arranged that, upon inhalation, a therapeutic agent is delivered by the device of the invention to an individual in a programmable manner so that the quantity and periodicity of the therapeutic agent can be varied according to a user's requirements.

17 Claims, 1 Drawing Sheet

INHALATION THERAPY

FIELD OF THE INVENTION

The invention relates to a device and corresponding method for controlling delivery of fluid to a dispensing apparatus.

A device as aforedescribed is used in a number of fields such as, for example, the medical field and the invention has particular, but not exclusive, application to the medical field wherein the device is used for controlling drug delivery to a nebuliser, face mask or any other dispensing apparatus and in particular respiratory dispensing apparatus.

BACKGROUND TO THE INVENTION

It is well known to use a nebuliser or face mask to deliver therapeutic drugs to the respiratory system. This is usually for the purpose of treating diseases such as asthma. In addition therapeutic agents may be administered by intubation. This method is typically used for treating ARDS (Adult Respiratory Distress Syndrome).

The use of the invention as a means of treating individuals suffering from ARDS will now be described, but it is not intended that the invention should be limited to such use.

ARDS may sometimes result from direct injury to the lungs (for example, from aspiration of gastric contents, pneumonia, or inhalation of a toxic substance); ARDS may also be caused by a systemic disorder (such as Sepsis) or alternatively by a drug reaction. Occasionally, multiple factors are involved. The syndrome develops in as many 150,000 Americans annually. Since ARDS was first described, the mortality rate among patients has remained relatively constant at about 50%. However, the usual cause of death has changed from hypoxia to multi-organ dysfunction. Therapy is supportive, consisting primarily of mechanical ventilation and positive end-expiratory pressure to decrease hypoxemia.

It has recently become clear that the mechanical abnormalities associated with ARDS are not homogeneously distributed throughout the lungs. The lungs are functionally small and in essence, a patients' lungs can be divided into areas that are infiltrated, consolidated, or collapsed (and thus poorly aerated and poorly compliant) and regions that have nearly normal levels of compliance and ventilation. In the early stages of ARDS, these regions are not fixed; even simple actions, such as moving from a supine to a prone position, can alter the location of aerated and non-aerated regions. As the disease progresses, these regions become increasingly fixed.

In healthy lungs, blood is shunted away from poorly aerated regions. In lungs affected by ARDS, poorly aerated regions continue to be perfused. A substantial mis-match between ventilation and profusion may develop leading to hypoxemia. The immediate (but not the sole) cause of poor aeration is pulmonary odema due to a generalised defect in capillary-membrane permeability. This defect may cause simultaneous dysfunction of other organs as well. Although it is incompletely understood, the capillary defect is believed to be produced by an array of inflammatory mediators, including cytokines, complement, and arachidonate metabolites. These mediators damage the endothelium and allow fluid and proteins to leak across it. In the early stages of ARDS odema is confined to the interstitium; later, however, it may enter the alveoli.

Additional physiological effects of these mediators include vasoconstriction and platelet aggregation, both of which may decrease blood flow to aerated regions of the lungs. Neutrophil-derived proteases and oxygen radicals may damage lung tissue directly. Abnormalities of surfactant may also develop. In the later stages of ARDS, fibrosis may occur. Clinically, these changes are manifested as increases in pulmonary-artery pressure and pulmonary vascular resistance. This creates a therapeutic dilemma. If systemic vasodilators are administered to decrease pulmonary vascular resistance, the likelihood that hypotension will develop is increased.

Similarly, the use of mechanical ventilation and positive end-expiratory pressure may sometimes increase the alveolar injury associated with ARDS by causing hyperinflation in compliant regions of the lungs. Thus, it is conceivable that because of the heterogeneity of lung injuries in ARDS, alveolar injury may be sustained—or even exacerbated—by the treatment intended to compensate for it. In a study by Rossaint et al ten patients with severe ARDS, received inhaled nitric oxide, a potent gaseous vasodilator, in all patients, pulmonary-artery pressure and pulmonary vascular resistance decreased significantly, while systemic arterial pressure and systemic vascular resistance were unaffected. In contrast, the administration of prostacyclin to nine patients produced marked decreases in levels of all four variables.

Site specific therapeutic agents are therefore desirable but not always available. However, selective administration of therapeutic agents increases the likelihood that a given agent will act at a target site. Thus, respiratory agents may be administered via the process of inhalation, so ensuring that the agent reaches directly its target site.

Therapeutic agents such as vasodilators are used to treat the above mentioned diseases.

It had long been recognised that directly acting vasodilators, such as glyceryl trinitrate and sodium nitroprusside act as nitric oxide donators. The action of the nitric oxide is to relax vascular smooth muscle. Indeed, nitric oxide mediates the vasodilator action of acetylcholine in animal and human pulmonary vessels, and appears to act as a braking mechanism against pulmonary vasoconstriction. Release of nitric oxide from endothelial cells in the pulmonary circulation appears to counteract hypoxic vasoconstriction; further, nitric oxide release is apparently decreased in hypoxia. There is circumstantial evidence that nitric oxide release from pulmonary vessels may be impaired in patients with chronic obstructive pulmonary disease (COPD). Inhalation of nitric oxide has been shown to cause selective pulmonary vasodilation in patients with pulmonary hypertension.

It is clear that nitric oxide may have a very important regulatory role in airway function and there has recently been much interest in nitrovasodilators. New nitric oxide donors, such as S-nitrothiols may have advantages when used to treat respiratory disorders.

Inhalation of nitric oxide by patients with sever ARDS reduces the pulmonary-artery pressure and increases arterial oxygenation by improving the matching of ventilation with perfusion, without producing systemic vasodilation. The vasodilatory effect of nitric oxide should, as mentioned, be limited to the ventilated regions of the lung when it is given by inhalation. In contrast to intravenously administered vasodilators, inhaled nitric oxide should selectively improve the perfusion of ventilated regions, thus reducing intrapulmonary shunting and improving arterial oxygenation.

It is clear from the above that nitric oxide is a useful therapeutic agent for the treatment of respiratory disorders.

It is clearly essential that the correct dose of any therapeutic drug including vasodilators is delivered to the patient. Currently, when administering respiratory drugs, a nebuliser or face mask is used and a continuous supply of drug is fed to the nebuliser or face mask resulting in an excessive and wasteful use of the drug. With the increase in patients suffering from asthma, together with patients diagnosed as having ARDS and other respiratory diseases, there is plainly a need for a device for controlling the delivery of therapeutic respiratory drugs.

It is therefore an object of the invention to provide a device that controls not only the amount of therapeutic agent administered but also the manner in which said agent is administered, thus providing for a more effective and at the same time more efficient device. The invention therefore concerns a device and corresponding method for controlling the delivery of therapeutic respiratory agents to a patient.

SUMMARY OF THE INVENTION

According to the invention there is therefore provided a device for use in controlling the delivery of therapeutic agents characterised in that it comprises:

a respiratory dispensing means to which is attached;

a first delivery means through which at least one therapeutic fluid can selectively flow; and a second delivery means through which a respiratory fluid can reversibly flow; and characterised in that said respiratory dispensing means includes a sensor adapted to monitor respiratory cycles of an individual and wherein said sensor is connected to a flow control means which is adapted to control the flow of fluid through, at least, said first delivery means, whereby upon detection of a predetermined point in a respiratory cycle, or sequence of cycles, said flow control means enables fluid to through said first delivery means so that therapeutic fluid is delivered to a patient for a pre-determined interval of time.

In a preferred embodiment of the invention said pre-determined point in a respiratory cycle is selected so that therapeutic fluid is delivered to a patient at the beginning of a respiratory cycle, that is upon inhalation.

Preferably, said pre-determined point in a respiratory cycle is at the beginning of a respiratory cycle or upon inhalation.

In this document the term respiratory cycles includes respiratory cycles or respiration which is both natural and artificial. Thus the invention has application in the controlled delivery of therapeutic agents to individuals who can breathe naturally and to individuals who require, partially or wholly, assisted ventilation. Accordingly, the device of the invention may include, in the instance where an individual is to receive assisted ventilation, artificial ventilation means so that delivery of the therapeutic agent occurs by intubation or the like.

A device in accordance with the invention therefore ensures that the flow of therapeutic fluid is delivered in a modulated fashion having regard to the respiratory cycle of an individual.

Ideally, when the therapeutic agent is nitric oxide, a bolus of therapeutic fluid (NO) is administered to a patient at the beginning of a respiratory cycle in a clinically effective concentration.

In a preferred embodiment of the invention said second delivery means is open to the atmosphere and is further provided with a two-way valve so as to allow fluid to flow through same upon inhalation and exhalation.

Preferably a supply means is connected to the first delivery means which supply means contains a pre-determined amount of at least one therapeutic agent.

In yet a further preferred embodiment of the invention the sensor comprises a thermistor which is electrically connected to the flow control means. The flow control means can be programmed in a manner whereby its response to the respiratory cycle of an individual can be varied so that, for example, the administration of a therapeutic fluid may occur once every one to the nth respiratory cycle. Alternatively, the flow control means may operate in a timed manner so that the flow of therapeutic fluid may occur once every pre-determined interval of time such as, for example, once every nth minute or nth hour or the like.

Preferably the respiratory dispensing means comprises a nebuliser, face mask or any other inhalation device.

In a yet further preferred embodiment of the invention a pump means is connected to the first delivery means so as to ensure that the fluid flows under positive pressure into the respiratory dispensing means under the control of the fluid control means.

In an alternative embodiment of the invention a pump means is also connected to the second delivery means so as to control the respiratory cycle of an individual.

In yet a further preferred embodiment of the invention the first delivery means includes an exhaust port so that compressed gas or gases or air, or a mixture thereof, can escape between deliveries of therapeutic fluid.

DESCRIPTION OF THE PREFERRED EMBODIMENT

Figure 1:
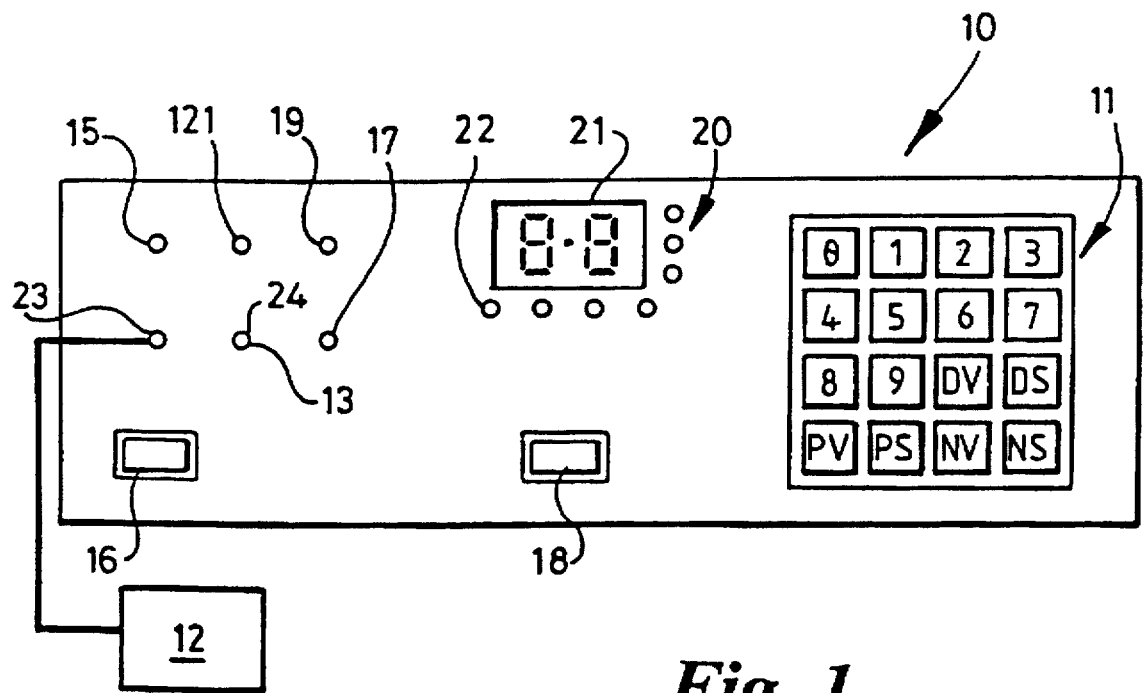
FIG. 1 is a diagrammatic representation of the system for controlling the delivery of therapeutic drugs.
Figure 2:
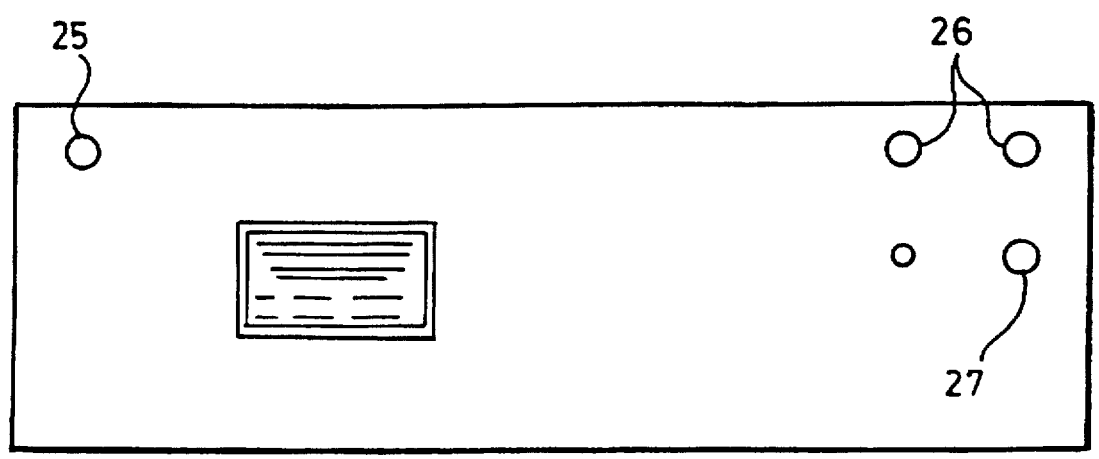
FIG. 2 is a rear view of the control panel.

FIG. 1 shows the control system which includes a compressed air supply 12 which enters a control device generally indicated by reference 10. Device 10 has a data entry keyboard generally indicated by reference 11 which is used to input information concerning the delivery of a therapeutic agent or drug. Compressed air, having passed from the air output 12 and having passed through the control device 10 is conducted via compressed air outlet 13 to the delivery device, for example, a nebuliser (not shown) for use by a patient. The system provides a continuous flow of compressed air through the nebuliser when the system is switched on.

The nebuliser includes a sensor which is adapted to monitor the respiratory cycle of a patient. Such a sensor may detect fluid flow, pressure change or temperature change and ideally is a heat sensor such as a thermistor. In use, when the patient inhales, cool air is drawn into the nebuliser and flows over the thermistor. On detection of cool air by the thermistor an electronic signal is passed to control device 10. A valve sited between the thermistor and nebuliser is then opened by the control device 10 to allow a mixture of compressed air and therapeutic drug to be allowed to pass into the nebuliser and delivered to the patient. The timing and geometry of the device is such that, when nitric oxide is administered, a bolus of nitric oxide is delivered to the patient at the beginning of a respiratory cycle ie upon inhalation and preferably at the beginning of each respiratory cycle. Moreover, the nitric oxide is delivered at a clinically effective concentration such as 5–100 ppm depending upon circumstances. For example, there may be an initial concentration of 40 ppm followed by a maintenance concentration of 10 ppm.

The control device 10 will now be described in detail. The thermistor is electrically connected to device 10 via socket 15. Device 10 includes three switches; a mains power switch 16, a purge switch 17 and a reset switch 18. The purge switch 17 opens the afore mentioned valve to flush out the nebuliser by producing a continuous flow of compressed air through the nebuliser. The reset switch 18 starts or halts a programmed sequence of delivery of a therapeutic agent. In addition, a sensor switch 19 is provided for starting the device if the sensor fails to detect inhalation, as described hereinafter.

The data entry keyboard 11 is used to input or change delivery parameters. The numbered keys allow the appropriate periods to be entered. In addition, command keys are provided and have the following functions; DV is used to view the pre-set delivery time; DS is used to set a new delivery time; PV is used to view the pre-set pause time and PS is used to set a new pause time; the NV key allows viewing of the pre-set number of events and NS allows a change to the number of deliveries.

Function indicators generally shown by reference 20 illustrate which parameter is being displayed on the LED display 21.

There are currently four status indicators, indicated generally by 22, each of which have the following meanings:

READY: Standby mode, the controller is waiting for instructions;

RUN: The system is active, waiting for an intake of breath, or RESET switch to be pressed;

PAUSE: Indicates the system is in pause mode;

END: Controller is delivered the present number of events and is waiting for further instructions.

The control device 10 is designed to deliver a predetermined dose of a therapeutic or pharmacological agent to a patient. Device 10 allows the following parameters to be programmed, via the keyboard 11.

a. Delivery (or event) time, 0.1–9.9 seconds;

b. Interval between events, 0.1–9.9 seconds;

c. Number of events, 1–99;

d. Delay time from inspiration to bulb operation, 0–9.9 seconds.

Device 10 has pre-set settings for these four variables which are:

i. 1.0 second EVENT time;

ii. 4.0 seconds PAUSE time;

iii. 5 EVENTS;

iv. 0 seconds DELIVERY DELAY time.

Use of the device according to the above specified pre-set settings results in the delivery of a therapeutic agent at the beginning of inspiration for a period of 1.0 second followed by an interval of 4 seconds before the whole cycle is repeated for a further four times; resulting in a regime represented by 5 EVENTS in total. Clearly, the number of times the cycle is repeated can be varied by varying the number of events up to a maximum of 99. Thereafter the device must be RESET as described hereinafter. Moreover, having regard to the duration of a respiratory cycle, the above specified parameters results in the administration of therapeutic agent in a short pulse at the beginning of a respiratory cycle.

Device 10 also has a number of built-in safety features to avoid incorrect operation. The valve within the control device has an exhaust port to allow the compressed air to escape between deliveries.

There are two modes of operation of the control device, a first without a delivery delay time and an second having a delivery delay time.

The first mode will now be described in detail. A sensor is either provided integral with or attached to a nebuliser and a mouthpiece. The sensor must be handled with extreme care and objects, for example, fingers, should not be inserted into the body of the sensor. As mentioned above, the sensor is connected at socket 15. An input air line, from the compressed air supply 12, is attached to a hose connector at 23 and an output line is connected from the output connector 24 to the nebuliser.

The device which is connected to a power supply is switched on at 16 and the indicators 20, 22 around display 21 are illuminated and the display shows 8.8. These actions may be accompanied by an audible sound emanating from a sound device positioned inside the nebuliser. After one second, all of the indicators go out leaving the READY light 22 lit and the display showing zero.

The compressed air supply 12 is adjusted to provide a required flow rate. The RESET switch 18 is pressed to use the default settings for EVENT time, PAUSE time, and number of events. If any of these need to be changed, the procedure for data entry using the keyboard should be followed, this will be described later.

At this point, the RUN and NUMBER OF EVENTS indicators are lit. The display 21 shows the pre-set number of events. The control device is now in a waiting mode. It is activated further by either an intake of breath through the mouthpiece or use of the sensor switch 19. In response to either of these events, device 10 opens the valve and compressed air is passed to the nebuliser. Valve opening is represented by activation of the indicator 12.

After the pre-set delivery time interval, device 10 closes the valve shutting off the compressed air supply to the nebuliser. The PAUSE indicator is now lit and the device 10 controller enters a wait mode whose length is determined by the pre-set pause time interval. At the end of this interval, the PAUSE indicator is extinguished, and the number of events is shown on the display. The number of events shown on the display corresponds to the number of inhalations and therefore each successive display is increased or decreased by the integer one according to requirements. The control device enters a further waiting mode prior to the next intake of breath.

This pre-set sequence can be halted at any time by pressing the RESET switch 18. The nebuliser may be flushed out between inhalations by pressing the purge switch 17.

When the pre-set number of events have taken place, the RUN and NUMBER OF EVENTS indicators are extinguished and the READY and END indicators are lit. At this point, the previous delivery sequence may be repeated by pressing the RESET switch 18. Alternatively, new parameters can be entered into device 10 using keyboard 11 prior to initiating a second adjusted run; or the control device can be switched off.

During the READY period, the sensor and sensor switch 19 demonstrate no response. During the RUN sequence any information entered via the keyboard is not registered by the control device.

The second mode of operation will now be described. This second mode includes a delivery delay time. The initial steps to set the control device 10 repeated are until the control device enters a waiting mode prior to either a first intake of breath as aforementioned or activation of the sensor switch.

In response to either event, an audible sound may be heard as afore. After the programmed delivery delay interval, the valve is opened and compressed air is passed to the nebuliser. Valve operation is represented by the indicator 12. After the pre-set delivery time interval, the valve closes, shutting off the compressed air supply to the nebuliser. The PAUSE indicator is now lit, and the device 10 enters a wait mode whose length is determined by the pre-set pause time interval. At the end of this interval, the PAUSE indicator is extinguished and the number of events shown on the display is modulated by a factor of one as aforedescribed. The control device enters a further wait mode prior to the next intake of breath.

The remaining steps in the sequence are the same as the previous description.

Turning now to the data entry keyboard 11 of the control device 10. The function of each of the keys has already been described. Any value may be changed independently and parameters may be entered in any order. To view a programmed value the required key is pressed and the display will show the value including a decimal point if appropriate. When the key is released, the display will show zero.

When a new value needs to be set, the required key, DS, PV, PS, NV or NS, is pressed and the corresponding function indicator is illuminated with a decimal point if required. The numeric keys are used to enter appropriate digits. The first number appears on the right of the display. The second number also appears on the right, whilst the first scrolls to the left. The new value is shown for one second then the display returns to zero and the function indicator is turned off. If an attempt is made to enter a time of 0.0 seconds, or 00 number of events, the software rejects the value and this is indicated by a one second audible sound. If this occurs, the required value should be entered again.

To view the delivery delay time, the switch 25 in FIG. 2 on the rear of the control device is pressed. An audible sound is heard, the pause indicator 22 is lit and the display 21 shows the current delay in the form N.N seconds. If the switch 25 is released immediately, the display will return to displaying zero after a one second interval.

To set the delivery delay time, the switch 25 is held for one second, the audible sound will be heard again and a new delay time can be entered via the keyboard. The new value is displayed for one second, then the display returns to zero and the PAUSE monitor indicator is turned off. To cancel the delay, enter 00, this is the only circumstance at which 00 is allowed as an entry.

The control device and the sensor should not be autoclaved or sterilised by exposure to heat, radiation or any fluid. It may be wiped clean with a dry cloth. The sensor may be carefully exposed to a draught to remove any dust.

An advantage of this system is the economic use of therapeutic drugs. In prior art devices, even if a patient is not inhaling, the appropriate drug is introduced into the compressed air system and fed to a respiratory device. This is wasteful because the inhalation period represents only one-third of the respiratory cycle. Thus, the delivery of a drug by inhalation can be made during only one-third of the respiratory cycle it follows that control of drug delivery so that it corresponds to the period of inhalation results in use of only a third or less of the drug.

A further advantage of this system is that it is flexible and so allows a therapeutic agent to be administered at a predetermined point in a respiratory cycle and for a predetermined interval of time.

There are a wide variety of uses of this system to administer, for example, respiratory drugs antibiotics, bronchodilators and even DNAase for patients suffering from cystic fibrosis.

I claim:

1. A device for use in controlling the delivery of therapeutic agents comprising:

a respiratory dispensing means to which is attached;

a first delivery means through which at least one therapeutic fluid can selectively flow; and a second delivery means through which a respiratory fluid can reversibly flow; and characterised in that;

said respiratory dispensing means includes a senor adapted to monitor respiratory cycles of an individual and wherein said sensor is connected to a flow control means which is adapted to control the flow of fluid through, at least, said first delivery means, whereby in response to detection of a predetermined point in a respiratory cycle, or sequence of cycles, said flow control means enables fluid to flow through said first delivery means so that therapeutic fluid is delivered to a patient for a predetermined interval of time, wherein said predetermined point in a respiratory cycle is selected so that therapeutic fluid is delivered to a patient at the beginning of a respiratory cycle; and further wherein said predetermined interval of time represents a short fraction of the respiratory cycle so that a short pulse of therapeutic agent is delivered.

2. A device according to claim 1 wherein said predetermined point in a respiratory cycle is at the beginning of a respiratory cycle.

3. A device according to claim 1 wherein there is further provided a delay means so that said delivery of therapeutic fluid can be delayed following said detection.

4. A device according to claim 1 wherein said second delivery means is in fluid connection with the atmosphere.

5. A device according to claim 1 wherein said second delivery means is provided with a 2-way valve so as to allow fluid to flow through same upon inhalation or exhalation.

6. A device according to claim 1 wherein a supply means is connected to said first delivery means which supply means contains a predetermined amount of at least one therapeutic agent.

7. A device according to claim 1 wherein said sensor comprises a thermistor, which thermistor is electrically connected to said flow control means.

8. A device according to claim 1 wherein said flow control means is programmable such that it responds variably to the respiratory cycle of an individual thereby allowing variable control of the fluid flowing through at least said first delivery means.

9. A device according to claim 8 wherein said flow control means can be programmed in a manner whereby the administration of at least a therapeutic fluid may occur once every nth respiratory cycle.

10. A device according to claim 8 wherein said flow control means operates in a timed manner whereby the administration of at least a therapeutic fluid occurs once every pre-determined interval of time.

11. A device according to claim 1 wherein said flow control means controls a pump means, which pump means is connected to at least one of said delivery means so as to ensure that at least one of said fluids flows under positive pressure into said respiratory dispensing means.

12. A device according to claim 1 where said respiratory dispensing means comprises a nebuliser, face mask or other inhalation device.

13. A device according to claim 1 wherein said respiratory dispensing means comprises a means for artificial ventilation.

14. A method for delivering at least one therapeutic agent to the respiratory system of an individual comprising:

monitoring respiratory cycles of an individual;

detecting a predetermined point in a respiratory cycle, or predetermined sequence of cycles wherein said predetermined point is selected so that said therapeutic agent is delivered at the beginning of a respiratory cycle;

arranging for the delivery of at least one therapeutic agent to said individual for a predetermined interval of time in response to detection of said point wherein said predetermined interval is relatively short compared to the length of a normal respiratory cycle such that a short pulse of therapeutic agent is delivered at the beginning of a respiratory cycle; and repeating the above described series of events.

15. A method according to claim 14 wherein said predetermined point of a respiratory cycle is at the beginning of a respiratory cycle.

16. A method according to claim 14 which further includes delaying said delivery of said therapeutic agent following said detection.

17. A method according to claim 14 in which the said agent is a therapeutically effective concentration of gases nitric oxide or a nitric oxide releasing agent.

* * * * *